(12) United States Patent
Calhoun et al.

(10) Patent No.: US 8,349,795 B2
(45) Date of Patent: *Jan. 8, 2013

(54) RESORBABLE THIN MEMBRANES

(75) Inventors: Christopher J. Calhoun, San Diego, CA (US); Ralph E. Holmes, San Diego, CA (US); Kenneth K. Kleinhenz, Lakeside, CA (US)

(73) Assignee: MAST Biosurgery AG, Zurich (CH)

( * ) Notice: Subject to any disclaimer, the term of this patent is extended or adjusted under 35 U.S.C. 154(b) by 46 days.

This patent is subject to a terminal disclaimer.

(21) Appl. No.: 13/193,371

(22) Filed: Jul. 28, 2011

(65) Prior Publication Data

US 2011/0280917 A1 Nov. 17, 2011

Related U.S. Application Data

(60) Continuation of application No. 11/983,562, filed on Nov. 9, 2007, now Pat. No. 8,012,502, which is a division of application No. 10/631,980, filed on Jul. 31, 2003, now Pat. No. 7,592,017, which is a continuation-in-part of application No. 10/385,399, filed on Mar. 10, 2003, now Pat. No. 6,673,362, which is a continuation of application No. 09/805,411, filed on Mar. 12, 2001, now Pat. No. 6,531,146.

(60) Provisional application No. 60/231,800, filed on Sep. 11, 2000, provisional application No. 60/196,869, filed on Mar. 10, 2000, provisional application No. 60/408,393, filed on Sep. 4, 2002, provisional application No. 60/399,792, filed on Jul. 31, 2002.

(51) Int. Cl.
*A61K 38/18* (2006.01)
*A61K 38/30* (2006.01)
*A61K 38/00* (2006.01)
*A61K 38/22* (2006.01)

(52) U.S. Cl. ............ 514/7.6; 514/8.6; 514/1.1; 514/9.5
(58) Field of Classification Search .................. 424/435
See application file for complete search history.

(56) References Cited

U.S. PATENT DOCUMENTS

| | | |
|---|---|---|
| 3,636,956 A | 1/1972 | Schneider |
| 3,874,986 A | 4/1975 | Browall et al. |
| 4,464,320 A | 8/1984 | Saidla |
| 4,603,695 A | 8/1986 | Ikada et al. |
| 4,769,038 A | 9/1988 | Bendavid et al. |
| 4,955,907 A | 9/1990 | Ledergerber |
| 5,030,220 A | 7/1991 | Howland |
| 5,047,054 A | 9/1991 | Vijayan et al. |
| 5,227,412 A | 7/1993 | Hyon et al. |
| 5,270,300 A | 12/1993 | Hunziker |
| 5,380,329 A | 1/1995 | Elia et al. |
| 5,412,068 A | 5/1995 | Tang et al. |
| 5,437,672 A | 8/1995 | Alleyne |
| 5,508,036 A | 4/1996 | Bakker et al. |
| 5,525,646 A | 6/1996 | Lundgren et al. |
| 5,609,629 A | 3/1997 | Fearnot et al. |
| 5,626,861 A | 5/1997 | Laurencin et al. |
| 5,679,723 A | 10/1997 | Cooper et al. |
| 5,686,090 A | 11/1997 | Schilder et al. |
| 5,700,901 A | 12/1997 | Hurst et al. |
| 5,759,190 A | 6/1998 | Vibe-Hansen et al. |
| 5,776,195 A | 7/1998 | Derycke |
| 5,795,584 A | 8/1998 | Totakura et al. |
| 5,797,946 A | 8/1998 | Chin |
| 5,906,997 A | 5/1999 | Schwartz et al. |
| 5,932,539 A | 8/1999 | Stupp et al. |
| 6,005,162 A | 12/1999 | Constantz |
| 6,034,140 A | 3/2000 | Schwartz et al. |
| 6,113,640 A | 9/2000 | Tormala et al. |
| 6,132,668 A | 10/2000 | Baars et al. |
| 6,133,325 A | 10/2000 | Schwartz et al. |
| 6,136,333 A | 10/2000 | Cohn et al. |
| 6,153,252 A | 11/2000 | Hossainy et al. |
| 6,211,217 B1 | 4/2001 | Spinale et al. |
| 6,244,868 B1 | 6/2001 | Schappert |
| 6,280,473 B1 | 8/2001 | Lemperle et al. |
| 6,331,312 B1 | 12/2001 | Lee et al. |
| 6,333,029 B1 | 12/2001 | Vyakarnam et al. |
| 6,391,059 B1 | 5/2002 | Lemperle et al. |
| 6,451,373 B1 | 9/2002 | Hossainy et al. |
| 6,530,956 B1 | 3/2003 | Mansmann |

(Continued)

FOREIGN PATENT DOCUMENTS

EP 0224460 A2 6/1987

(Continued)

OTHER PUBLICATIONS

International Search Report and Written Opinion, Jul. 7, 2010, PCT/IB2009/006229.

(Continued)

*Primary Examiner* — Shengjun Wang
*Assistant Examiner* — Timothy E Betton
(74) *Attorney, Agent, or Firm* — Stout, Uxa, Buyan & Mullins, LLP

(57) ABSTRACT

Resorbable lactide polymer thin membranes are disclosed. The thin membranes are constructed of polylactide resorbable polymers, which are engineered to be absorbed into the body relatively slowly over time in order to reduce potential negative side effects. The membranes are formed to have very thin thicknesses, for example, thicknesses between about 0.010 mm and about 0.30 mm. The membranes can be extruded from polylactide polymers having a relatively high viscosity property, can be preshaped with relatively thick portions, and can be stored in sterile packages.

20 Claims, 10 Drawing Sheets

U.S. PATENT DOCUMENTS

| | | | |
|---|---|---|---|
| 6,531,146 | B2 | 3/2003 | Calhoun et al. |
| 6,596,267 | B1 | 7/2003 | Hubbell et al. |
| 6,673,362 | B2 | 1/2004 | Calhoun et al. |
| 6,719,795 | B1 | 4/2004 | Cornwall et al. |
| 7,074,239 | B1 | 7/2006 | Cornwall et al. |
| 7,537,782 | B2 | 5/2009 | Calhoun et al. |
| 8,012,502 | B2 * | 9/2011 | Calhoun et al. ............... 424/435 |
| 2001/0004693 | A1 | 6/2001 | Burkhead et al. |
| 2001/0056303 | A1 | 12/2001 | Caneiro et al. |
| 2002/0001609 | A1 | 1/2002 | Calhoun et al. |
| 2002/0173213 | A1 | 11/2002 | Chu et al. |
| 2003/0059463 | A1 | 3/2003 | Lahtinen |
| 2003/0185874 | A1 | 10/2003 | Calhoun et al. |
| 2004/0018175 | A1 | 1/2004 | Dimitrijevich |
| 2004/0030304 | A1 | 2/2004 | Hunt et al. |
| 2005/0074495 | A1 | 4/2005 | Schwartz et al. |
| 2005/0175665 | A1 | 8/2005 | Hunter et al. |
| 2008/0063686 | A1 | 3/2008 | Calhoun et al. |

FOREIGN PATENT DOCUMENTS

| | | | |
|---|---|---|---|
| EP | 1384450 | A1 | 1/2004 |
| JP | 7116241 | A | 5/1995 |
| JP | 2000503555 | A | 3/2000 |
| JP | 2000189509 | A | 7/2000 |
| JP | 2000265333 | A | 9/2000 |
| JP | 2000279433 | A | 10/2000 |
| JP | 2003103429 | A | 4/2003 |
| JP | 2007504227 | A | 3/2007 |
| JP | 2008033718 | A | 2/2008 |
| JP | 2008300481 | A | 12/2008 |
| WO | 9013302 | A | 11/1990 |
| WO | 9317635 | A1 | 9/1993 |
| WO | 9320859 | A1 | 10/1993 |
| WO | 9802171 | A1 | 1/1998 |
| WO | 9951163 | A1 | 10/1999 |
| WO | 0015270 | A1 | 3/2000 |
| WO | 0015273 | A1 | 3/2000 |
| WO | 0062707 | A2 | 10/2000 |
| WO | 0167987 | A1 | 9/2001 |

OTHER PUBLICATIONS

Supplementary European Search Report, Aug. 31, 2009, EP 03772191.

Supplementary European Search Report, Sep. 10, 2009, EP 05786506.

International Search Report and Written Opinion, Aug. 19, 2009, PCT/US09/49728.

Massie et al. "Antifibrotic Gels Versus a Barrier Sheet in the Prevention of Epidural Fibrosis Postlaminectomy" 2001, Presented at 16th Annual Meeting of North American Spine Society. (See "The Spine Journal" vol. 2, Issue 2, Supplement 1, Mar. 2002, 3 pages.).

Welch et al. "Use of Polylactide Resorbable Film as an Adhesion Barrier" Nov. 2002, Journal of Neurosurgery: Spine, vol. 97, pp. 413-422.

International Search Report and Written Opinion, Jan. 12, 2010, PCT/IB2008/003797.

International Search Report, Jun. 6, 2001, PCT/US01/07989.

International Search Report, Jan. 11, 2005, PCT/US03/23919.

International Search Report, Jan. 11, 2005, PCT/US03/24824.

International Search Report, Mar. 2, 2006, PCT/US05/28834.

Lee et al. "Prevention of Postlaminectomy Scar Formation" Spine, vol. 9, No. 3, 1984, pp. 305-312.

Maglio G et al. "Compatibilized poly (Epsilon-Caprolactone)/Poly(L-Lactide) Blends for Biomedical Uses" Macromol, Rapid Commun 20 No. 4, pp. 236-238 (1999).

Bendix "Chemical Synthesis of Polylactide and its Copolymers for Medical Applications" Polymer Degredation and Stability 59 (1998) pp. 129-135.

Gates "Controlled Drug Delivery Using Bioerodible Polymeric System for the Treatment of Periodontitis" Graduate Department of Pharmaceutical Sciences, University of Toronto (1999), printed pp. 1-173, especially p. 56.

* cited by examiner

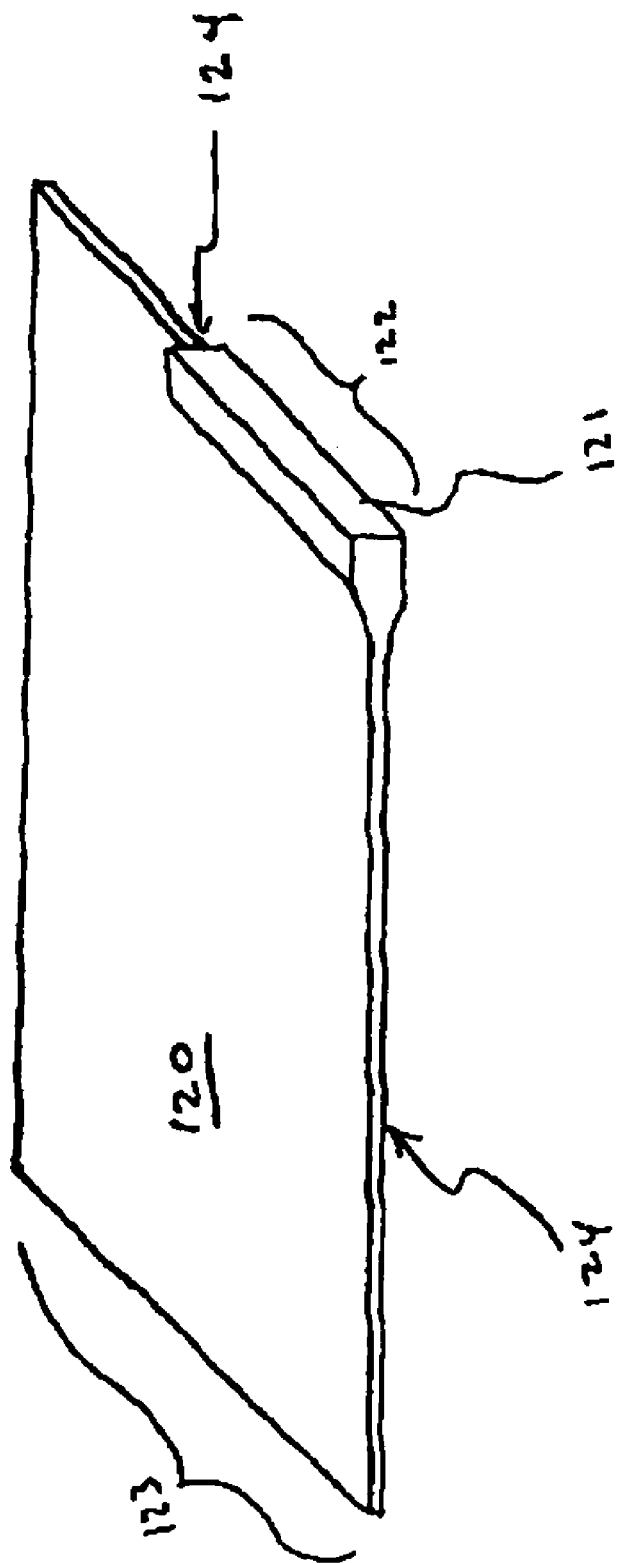

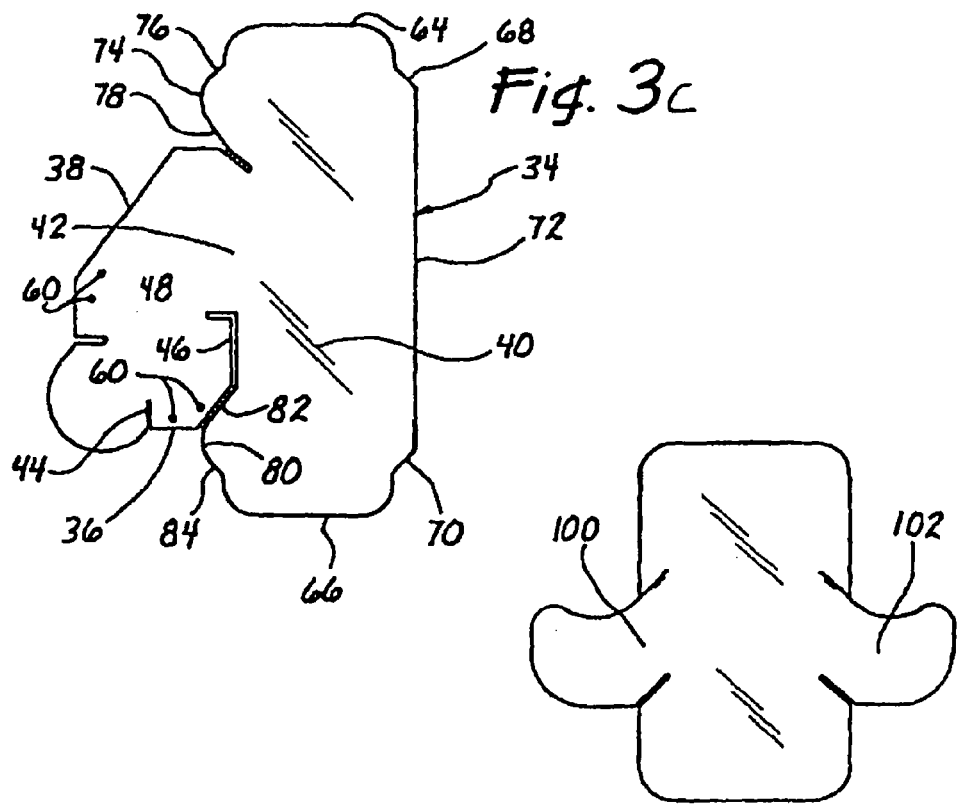
Fig. 3c
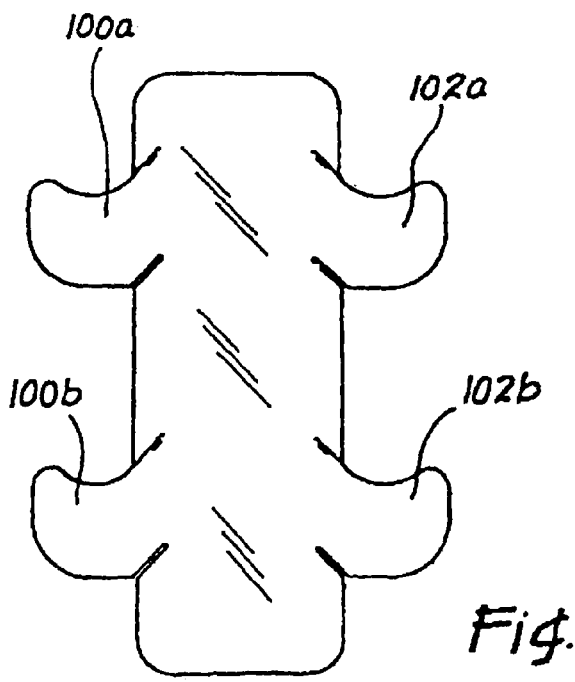
Fig. 4
Fig. 5

RESORBABLE THIN MEMBRANES

CROSS-REFERENCE TO RELATED APPLICATIONS

This application is a continuation of U.S. application Ser. No. 11/983,562, filed Nov. 9, 2007 now U.S. Pat. No. 8,012,502, which is a divisional of U.S. application Ser. No. 10/631,980, filed Jul. 31, 2003, now U.S. Pat. No. 7,592,017. U.S. application Ser. No. 10/631,980 is a continuation-impart of U.S. application Ser. No. 10/385,399, filed Mar. 10, 2003, now U.S. Pat. No. 6,673,362, which is a continuation of U.S. application Ser. No. 09/805,411, filed Mar. 12, 2001, now U.S. Pat. No. 6,531,146, which claims the benefit of priority of U.S. Provisional Application No. 60/231,800, filed Sep. 11, 2000, and of U.S. Provisional Application No. 60/196,869, filed Mar. 10, 2000. U.S. application Ser. No. 10/631,980 also claims the benefit of priority of U.S. Provisional Application No. 60/408,393, filed Sep. 4, 2002, and of U.S. Provisional Application No. 60/399,792, filed Jul. 31, 2002. The foregoing applications are commonly assigned and the contents of all are expressly incorporated herein by reference.

BACKGROUND OF THE INVENTION

1. Field of the Invention

The present invention relates generally to medical implants and, more particularly, to resorbable membranes and methods of using the membranes.

2. Description of Related Art

A major clinical problem relating to surgical repair or inflammatory disease is adhesion which occurs during the initial phases of the healing process after surgery or disease. Adhesion is a condition which involves the formation of abnormal tissue linkages. These linkages can, for example, impair bodily function, produce infertility, obstruct the intestines and other portions of the gastrointestinal tract (bowel obstruction) and produce general discomfort, e.g. pelvic pain. The condition can in some instances be life threatening. The most common form of adhesion occurs after surgery as a result of surgical interventions, although adhesion may occur as a result of other processes or events such as pelvic inflammatory disease, mechanical injury, radiation treatment and the presence of foreign material.

Various attempts have been made to prevent postoperative adhesions. For example, the use of peritoneal lavage, heparinized solutions, procoagulants, modification of surgical techniques such as the use of microscopic or laparoscopic surgical techniques, the elimination of talc from surgical gloves, the use of smaller sutures and the use of physical barriers (membranes, gels or solutions) aiming to minimize apposition of serosal surfaces, have all been attempted. Unfortunately, very limited success has been seen with these methods. Barrier materials, in various forms such as membranes and viscous intraperitoneal solutions, which are designed to limit tissue apposition, have also met with limited success. These barrier materials can include cellulosic barriers, polytetrafluoroethylene materials, and dextran solutions.

U.S. Pat. No. 5,795,584 to Tokahura et al. discloses antiadhesion or scar tissue reduction films or membranes, and U.S. Pat. No. 6,136,333 to Cohn et al. discloses similar structures. In the Tokahura et al. patent, a bioabsorbable polymer is copolymerized with a suitable carbonate and then formed into a non-porous single layer adhesion barrier such as a film. In the Cohn et al. patent, a polymeric hydrogel for anti-adhesion is formed without crosslinking by using urethane chemistry. Both of these patents involved relatively complex chemical formulas and/or reactions resulting in particular structures for use as surgical adhesion barriers. There continues to be a need to for an improved membrane.

SUMMARY OF THE INVENTION

The present invention provides an improved resorbable thin membrane that can be used in various surgical contexts, for example, to retard or prevent tissue adhesions and reduce scarring. Furthermore, the polymers and co-polymers of the present invention require relatively simple chemical reactions and formulations.

In accordance with one feature of the present invention a resorbable thin membrane is provided comprising a substantially uniform composition of an amorphous polylactide, for example, a 70:30 poly (L-lactide-co-D,L-tactide).

The amorphous polylactide membrane can be formed by extrusion at an initial, relatively high viscosity property which is at or greater than about 5.5 g/dL. The initially high viscosity property may facilitate reliable formation of the membrane by attenuating the occurrence of, for example, breaking or tearing of the membrane, during the extrusion process. After processing and sterilization, the viscosity property of the membrane will typically be lower. Other relatively high viscosity properties, such as those above 4 g/dL can be used according to other aspects of the invention, in order to increase the strength of the amorphous polylactide material during the extrusion process. The extrusion process provides the membrane with a biased molecular orientation.

According to another feature of the invention, a membrane has a first substantially-smooth surface and a second substantially-smooth surface, is non-porous, and is about 0.01 mm to about 0.300 mm thick as measured between the first substantially-smooth surface and the second substantially-smooth surface. The membrane comprises at least one relatively thick portion, which can form at least a segment of an edge of the membrane. The membrane thus has a varying cross-sectional thickness.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 3b is an enlarged view of FIG. 3a;

FIG. 3c illustrates a thin membrane for application to the exiting nerve root of the spinal chord in accordance with a first pre-formed embodiment of the present invention;

FIG. 4 illustrates a thin membrane for application to two exiting nerve roots of the spinal chord in accordance with a second pre-formed embodiment of the present invention; and FIG. 5 illustrates a thin membrane for application to four exiting nerve roots of the spinal chord in accordance with a third pre-formed embodiment of the present invention.

DETAILED DESCRIPTION OF THE PRESENTLY PREFERRED EMBODIMENTS

Figure 1A:
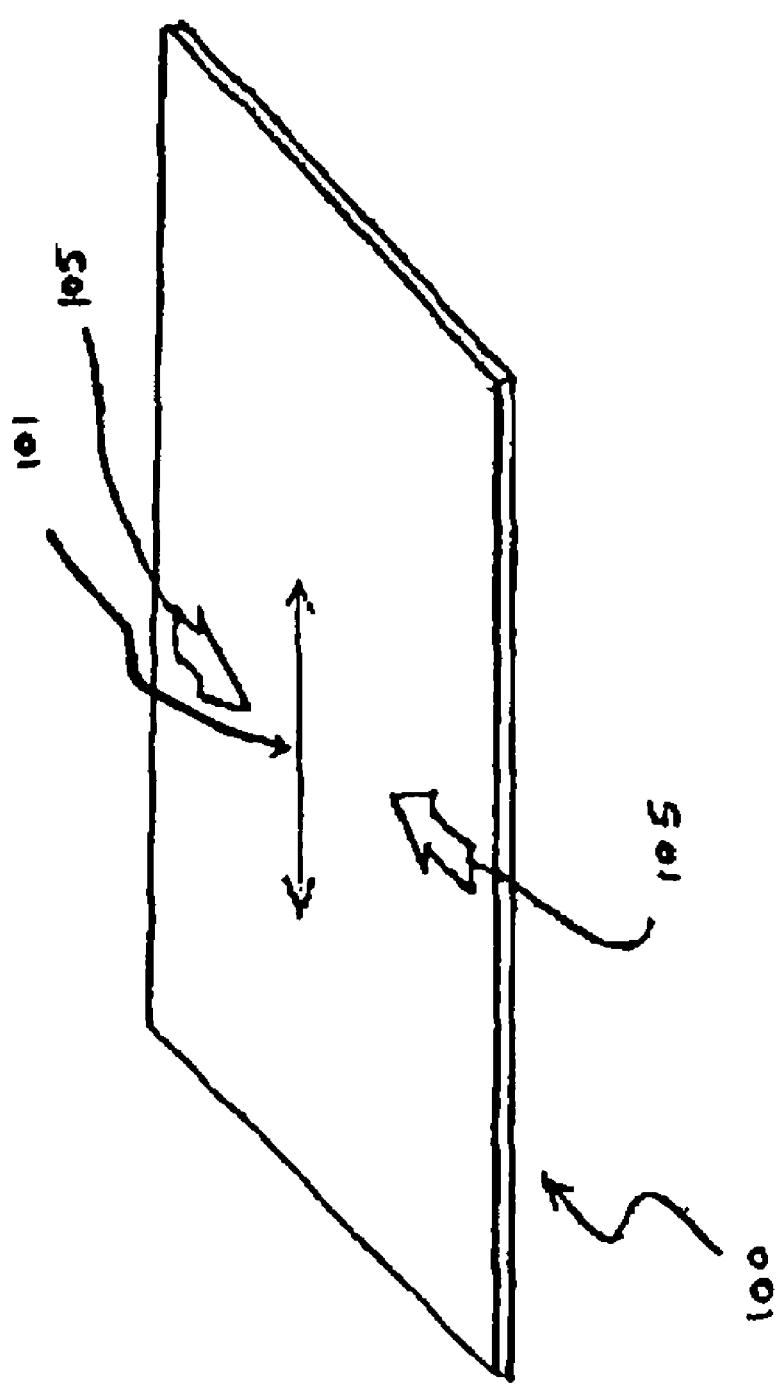
FIG. 1a illustrates a thin membrane, wherein a molecular orientation of the amorphous polylactide is biased on an axis.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims.

A resorbable thin membrane in accordance with one embodiment of the present invention comprises a substantially uniform composition comprising a polylactide. In the illustrated embodiment, the polylactide is amorphous and/or has a biased molecular orientation. As used herein, amorphous polylactides are those which do not yield sharp X-ray diffraction diagrams. These polymers can contain few, if any, regions in which the structural units are arranged in three-dimensional regular (crystalline) order; and their structure may be visualized as a tangle of long molecules in which there may be groups of roughly parallel but insufficiently ordered sections of chains. In one embodiment, the phrase "substantially amorphous" can be substituted herein for the term amorphous, and in another embodiment the phrase "somewhat amorphous" or "slightly amorphous" can be substituted herein for the term amorphous.

Barrier membranes of the present invention may be constructed from various biodegradable materials, such as resorbable polymers. In accordance with one embodiment, non-limiting polymers which may be used to form barrier membranes of the present invention include polymers (e.g., copolymers) of lactide (L, D, DL, or combinations thereof), glycolide, trimethylene carbonate, caprolactone and/or physical and chemical combinations thereof. In one embodiment, the barrier membranes comprise a polylactide, which can be a copolymer of L-lactide and D,L-lactide. For example, the copolymer can comprise about 60-80% of L-lactide and about 20-40% of D,L-lactide, and in a preferred embodiment the copolymer comprises a 70:30 poly (L-lactide-co-D,L-lactide). In one embodiment, the barrier membranes are formed by polymers homo and/or copolymers) derived from one or more cyclic esters, such as lactide (i.e., L, D, DL, or combinations thereof), epsilon-caprolactone and glycolide. For instance, the barrier membranes in one embodiment can comprise about 1 to 99% epsilon-caprolactone, or in another embodiment can comprise 20 to 40% epsilon-caprolactone. In one example, a barrier membrane comprises 65:35 poly (L-lactide-co-epsilon-caprolactone). In other embodiments, butyrolactone, valerolactone, or dimethyl propiolactone can be used with or as a substitute for epsilon-caprolactone. In another embodiment, the barrier membranes can comprise a copolymer including lactide and glycolide which is resorbed into the body more rapidly than the above-mentioned poly (L-lactide-co-D,L-lactide).

In a presently preferred embodiment, the thin membranes can be manufactured using extrusion procedures, such as for example those known in the art. The extrusion procedures advantageously can provide for efficient production of the membranes. Moreover, membranes which are manufactured by such extrusion techniques can be free from solvent trappings in the membrane and, furthermore, can be provided with a molecular bias, including a predetermined molecular bias. Monoaxial extrusion may be employed to manufacture the membranes in a preferred embodiment of the present invention. In a modified embodiment, biaxial extrusion procedures may be implemented to manufacture the membranes. In one embodiment, a composition mixture comprising an amorphous resorbable polymer, such as an amorphous lactide polymer, which can be for example poly L-lactide or more preferably poly (L-lactide-co-D,L-lactide), is extruded to form a membrane of the present invention. In one embodiment, poly (L-lactide-co-D,L-lactide) 70:30 Resomer LR708 (manufactured and supplied from Boehringer ingelheim KG of Germany) is extruded to form membranes of the present invention.

In accordance with one aspect of the present invention, the membranes have a particular range of a viscosity property. As used herein, a "viscosity property" is a measure of the viscosity of a polymeric dilute solution viscosity, expressed as the ratio of the natural logarithm of the relative viscosity to the concentration of the polymer in grams per 100 milliliters of solvent. Viscosity property may be understood by persons of skilled in the art to be the inherent viscosity of a solution, as conventionally used in the art. In one embodiment, the membranes of the present invention have a molecular bias, indicating they were formed from an extrusion technique, and a relatively high viscosity property.

In accordance with one aspect of the present invention, it is discovered that an amorphous polylactide composition having a pre-extrusion viscosity property greater than about 5 g/dL, can be extruded to form the relatively thin membranes of the present invention. Other relatively high viscosity properties, such as those above 4 g/dL, can be used according to other aspects of the invention, in order to increase the strength of the amorphous polylactide material during for example the extrusion process.

The initially high (i.e., pre-extrusion) viscosity property of the amorphous polylactide may facilitate reliable formation of the membrane by for example attenuating an occurrence of weakening, breaking or tearing of the membrane, during the extrusion process. Although after processing and sterilizing the viscosity property of the membrane is lower, the initial relatively high viscosity property of the membrane can advantageously facilitate extrusions down to a thickness on the order of fractions of a millimeter. For example it is discovered that an amorphous polylactide polymer having an initial (pre-extrusion) viscosity property within a range of about 5 g/dL to about 7 g/dL may be extruded to form a membrane, having a thickness of about 0.02 mm and a resulting viscosity property of about 2.5 g/dL to about 3.5 g/dL with the use of sterilizing techniques that do not significantly change the viscosity property of the material. In one embodiment, ethylene oxide is used for sterilizing the thin membranes. It is believed that ethylene oxide does not cause a substantial reduction in the viscosity property of the thin membrane. In other embodiments wherein other sterilizing techniques are used, such as electron-beam, the resulting viscosity property may be about 1.25 g/dL to about 1.75, instead about 2.5 g/dL to about 3.5 g/dL. In other embodiments, such as wherein electron-beam sterilization is used, the extruded membranes can have viscosity properties greater than about 1 g/dL. In one embodiment, the membranes have a viscosity property greater than about 2 g/dL. Preferably, the membranes of the present invention have a viscosity property of about 2.7 g/dL to about 3.5 g/dL.

In accordance with one aspect of the invention, the molecular orientations of the amorphous polylactides can be biased. The above-discussed extrusion process can provide such biased molecular orientations. The biased molecular orientations may be predetermined so that a suitable process, such as a suitable extrusion process, may be employed in the manufacture of the membranes disclosed herein. In one embodiment, polymer chains of the membrane are substantially aligned on one axis, as shown in FIG. 1a. For example, more than about 65% and preferably more than about 80% of the polymer chains or segments of polymer chains are aligned on an axis 101 of a thin membrane 100.

Figure 1B:
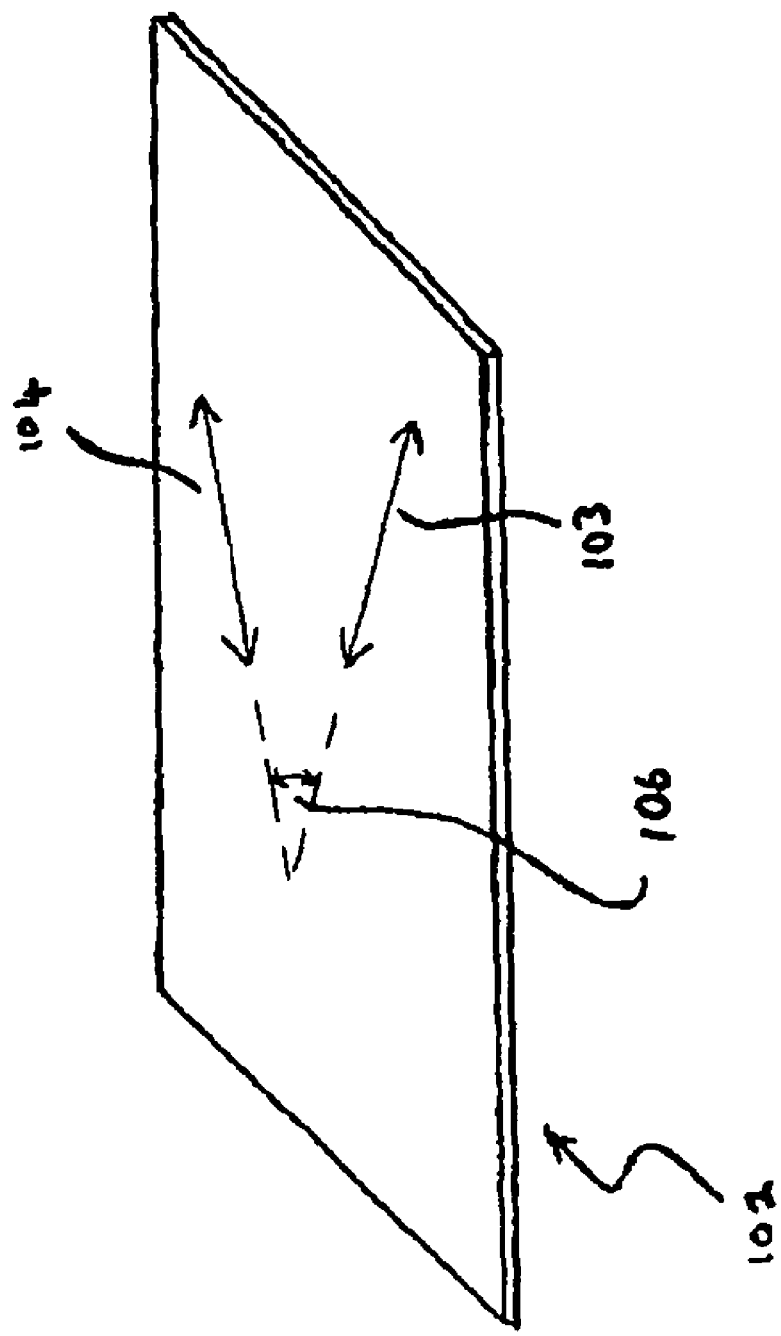
FIG. 1b illustrates a thin membrane, wherein the molecular orientation of the amorphous polylactide is biased toward two axes.

In one embodiment, the polymer chains are substantially aligned on two axes. FIG. 1b shows a membrane 102 having both a first axis 103 and a second axis 104 on which the polymers are aligned. In such an embodiment, more than about 50%, preferably more than about 90%, of the polymer chains or segments of polymer chains are substantially aligned on one of the two axes. In one embodiment, the aligned polymers are equally proportioned between the first axis 103 and the second axis 104. In another embodiment, the aligned polymers lie more on the first axis 103 than the second axis 104. For example the polymers can be about 45% aligned on the first axis and about 55% aligned on the second axis. In one embodiment, the axes form an angle 106 of less than 80 degrees. Preferably, the axes form an angle 106 of less than about 45 degrees, more preferably less than 30 degrees, and even more preferably less than 20 degrees.

The molecular orientations of the amorphous polylactides can confer various physical characteristics to the membrane. For example, when subjected to heat treatment sufficient to bring the membrane to its glass transition temperature, a membrane having a biased molecular orientation may shrink in the direction substantially perpendicular to an axis. As shown in FIG. 1a, when the membrane 100 having a biased molecular orientation is subjected to heat treatment, the direction of shrinkage 105 may be substantially perpendicular to the axis 101. In addition, the biased molecular orientation may permit the direction of shrinkage to be controlled or selectively controlled when the membrane is heated. This may be advantageous in situations where specific configurations and sizes are desired for the implantation of the membranes.

In one embodiment, during an extrusion process a membrane is output through an orifice having a first thickness and, subsequently, the membrane is stretched down to a second thickness, wherein the first thickness is greater than the second thickness. The first thickness can be greater than two times the second thickness, more preferably greater than five times the second thickness, and more preferably greater than ten times the second thickness. Accordingly, when the processed and sterilized membrane is subsequently brought to its glass transition temperature, its thickness wilt or may return back to the first thickness.

In one embodiment, a membrane of the present invention does not shrink uniformly in all directions when it is subjected to heat treatment. Preferably, a membrane of the present invention shrinks substantially in a direction perpendicular to the molecular orientation axis or axes, and does not substantially shrink in the direction parallel to the molecular orientation axis, when brought to a glass transition temperature of the membrane. For example, a membrane of the present invention may shrink about 5% to about 30% in the direction perpendicular to the molecular orientation axis or axes, and my shrink about 1% to about 5% in the direction parallel to the molecular orientation axis. In one example, when the processed and sterilized membrane is subsequently brought to its glass transition temperature, it will shrink in a direction substantially perpendicular to the alignment axis (e.g., 101) or axes (e.g., 103, 104) in an amount proportional to the amount it was stretched in the initial extrusion process. As presently embodied, the shrinkage in the direction perpendicular to the alignment axis or axes will continue until a thickness of the membrane returns from the second thickness to the first thickness.

A membrane of the present invention can have at least one substantially smooth-surface. Preferably, a membrane of the present invention has two (opposing) substantially smooth surfaces. As measured between the opposing surfaces, a membrane of the present membrane can have a thickness of about 0.01 mm to about 0.3 mm and, more preferably, about 0.01 mm to about 0.1 mm. In a preferred embodiment, a membrane of the present invention has a thickness of about 0.015 mm to about 0.025 mm. In another preferred embodiment, a membrane of the present invention has a thickness of about 0.02 mm.

A membrane of the present invention may further comprise at least one thick portion protruding from at least one of the two substantially smooth surfaces. In a preferred embodiment, the at least one thick portion protrudes from both of the two substantially smooth surfaces. In other words, the membrane may include multiple regions or portions with different thicknesses. In one embodiment, the membrane includes a first portion having a first thickness, and a second portion having a second thickness, where the first thickness is greater than the second thickness. The first portion may be located away from an edge of the membrane, or the first portion may be located at the edge of the membrane. In addition, the first portion has a length which is not greater than the length or width of the membrane. In certain embodiments, the length is shorter than both the length and the width of the membrane.

The output orifice of the extruding device may have a shape which corresponds to a cross section of the membrane. For example, in order to generate a membrane having relatively thick portions on two opposing edges of the membrane, the output orifice of the extruding device may comprise a generally rectangular shape having a width and a height, wherein the shape is modified by the height of the output orifice being greater at the two opposing edges of the output orifice than in an area between the two opposing edges of the output orifice. In such a configuration, the profile of heights across the width of the output orifice roughly corresponds to the profile of thicknesses across the width of the thin membrane. In other embodiments, a thin membrane having for example thick portions on opposing edges thereof may be generated using an extrusion device having a rectangular output orifice. In other embodiments, the thick portion(s) may be formed by means, such as machining, which can be implemented alone or in combination with, for example, the above-discussed extrusion processes. In addition to the above processes which can generate monoaxial molecular alignments, wherein for example, 80% or more of the membrane molecular alignment is in one direction, a membrane having a biaxial molecular orientation may be generated using for example a circular output orifice wherein pressurized air is blown into a tubular, thin membrane outputted through the circular output orifice.

Figure 2A:
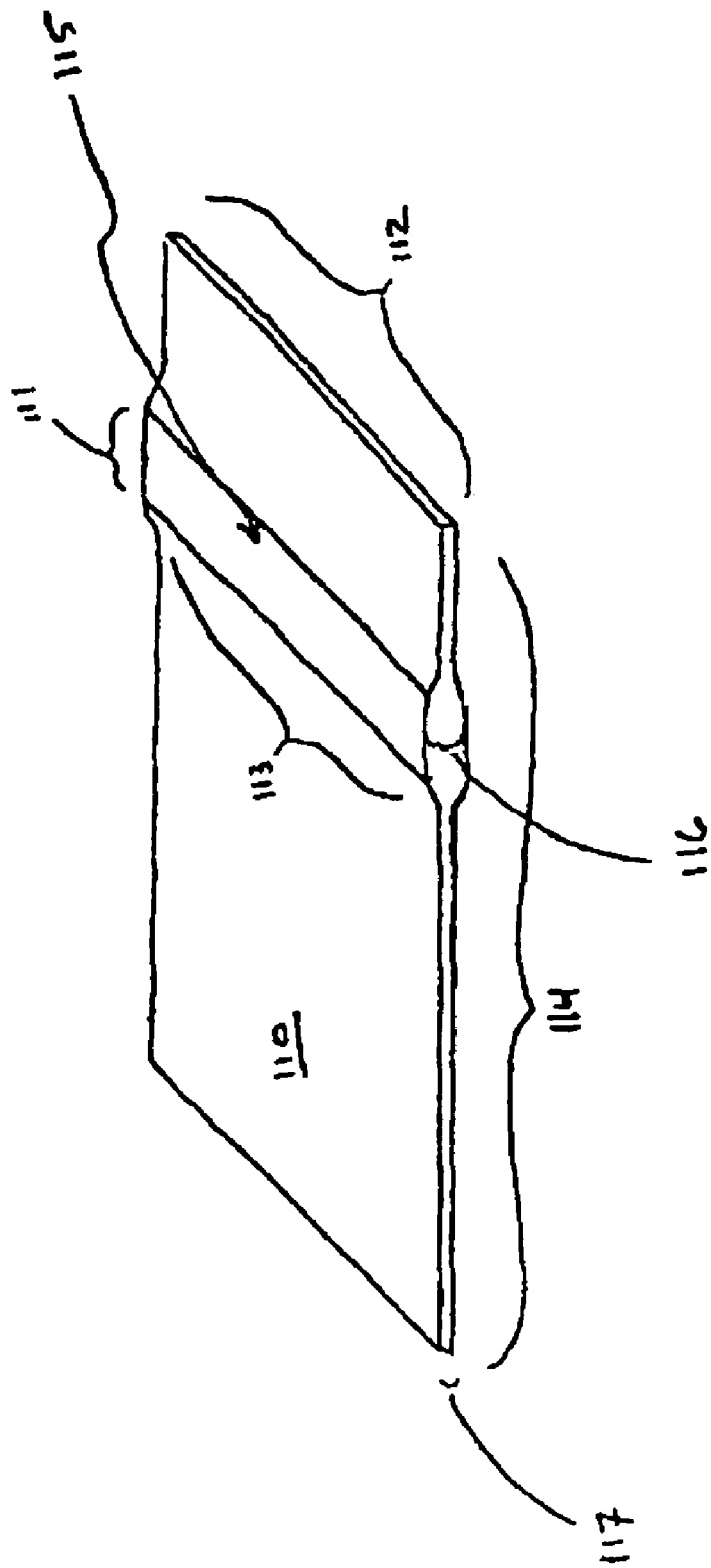
FIG. 2a illustrates a thin membrane having a thick portion.

Preferably, the thick portion is effective to provide an attachment function to the membrane. In modified embodiments, the thick portion may be effective to provide rigidity to at least a portion of the membrane. In one embodiment, each thick portion has a length equal to or less than a length of the membrane, a width of about 0.5 mm to about 25 mm and in one embodiment lot wider than the width of the membrane), and a thickness of about 2 to about 10 times thicker than the thickness of the membrane. For example, FIG. 2a shows a thick portion 115. In this figure, a length 113 of the thick portion 115 is equal to that of the length of the membrane 112, a width of the thick portion 111 is shorter than the width of the membrane 114, and a thickness of the thick portion 116 is about three times the thickness of the membrane 117. In view of the disclosure herein, thick portion 115 corresponds to a first portion having a first thickness, and the remaining portions attic illustrated membrane 112 correspond to a second portion having a second thickness which is less than the first thickness.

Figure 2C:
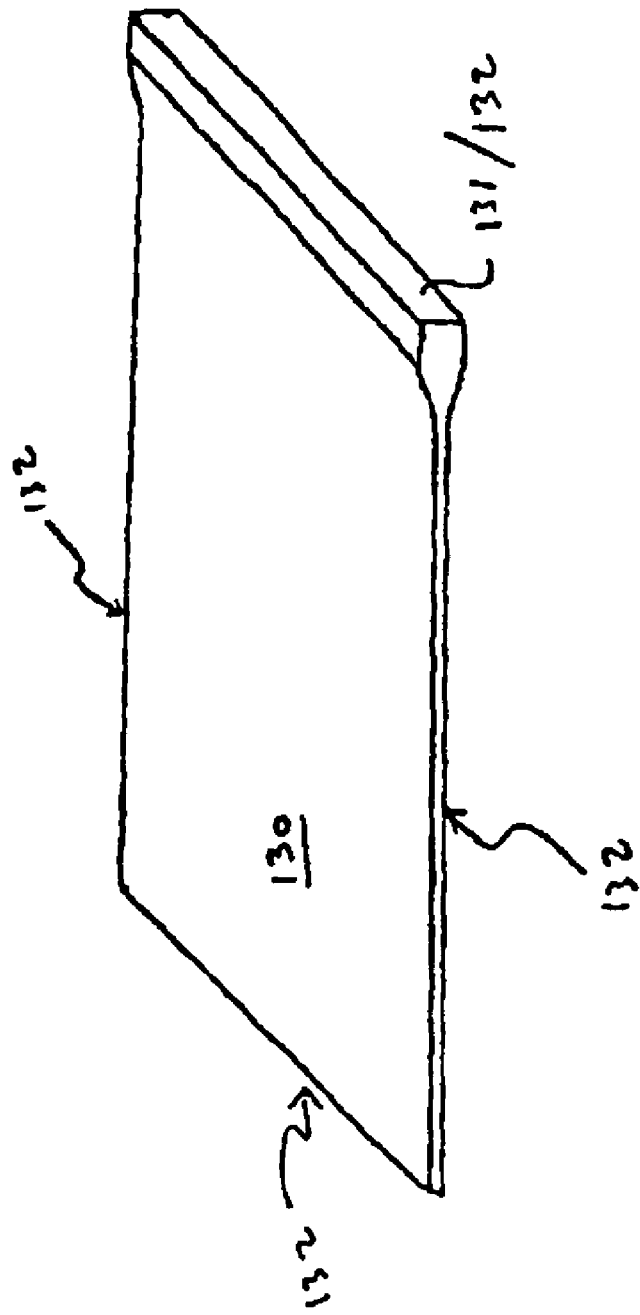
FIG. 2c illustrates a thin membrane having a thick portion forming an edge of the membrane.
Figure 2D:
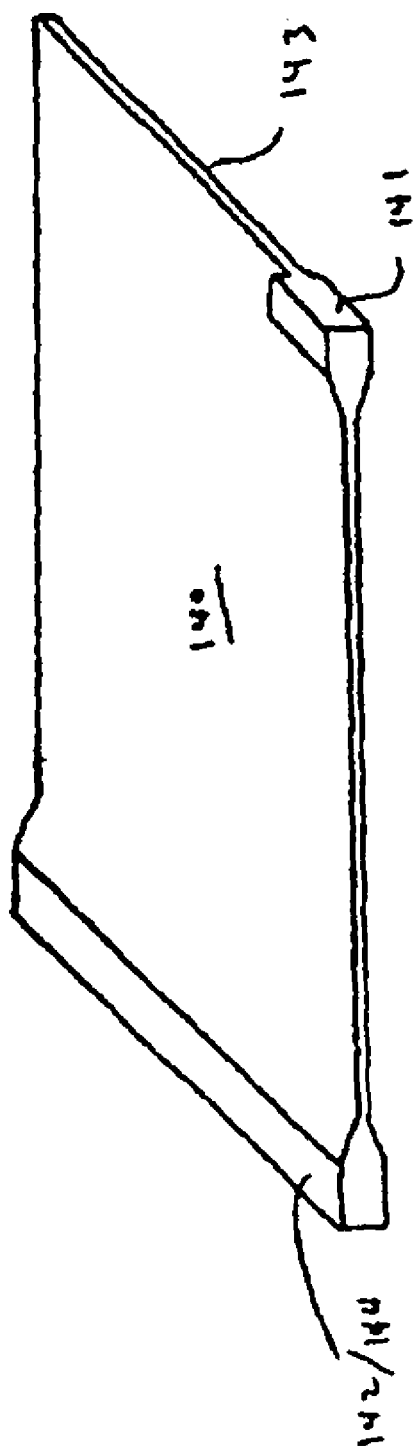
FIGS. 2d and 2e illustrate a membrane having more than one thick portion thereon.
Figure 2:
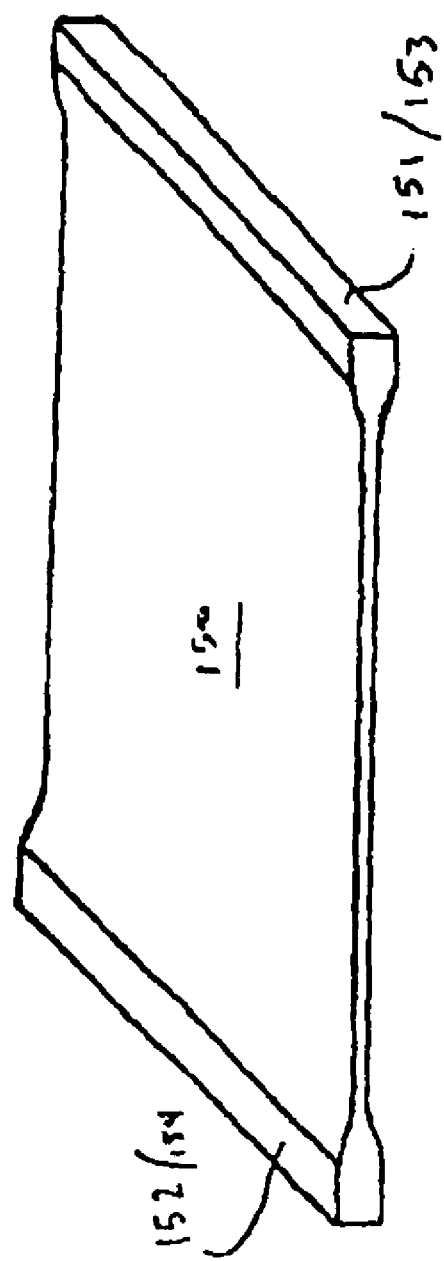
FIG. 2b illustrates a thin membrane having a thick portion forming a segment of an edge of the membrane.
FIG. 2f illustrates a membrane having thick portions with holes.

In one embodiment, the thick portion has a length shorter than that of the membrane. For example, FIG. 2b shows a membrane 120 comprising a thick portion 121. The length of the thick portion 122 is smaller than the length of the membrane 123. The length of the thick portion 122 is also smaller than the width of the membrane 123. In one embodiment, the thick portion forms a segment of an edge of the membrane or forms the entire edge of the membrane. For example, FIG. 2b shows a thick portion forming a segment of an edge of a membrane 124. FIG. 2c shows a membrane 130 having four edges 132, one of which is formed by a thick portion 131. In one embodiment, a membrane comprises more than one thick portion. For example, FIG. 2d shows a membrane 140 having a first thick portion 141 forming a segment of the first edge 143, and a second thick portion 142 forming a segment of the second edge 144.

A preferred thin membrane of the present invention comprises a substantially uniform composition of an amorphous polylactide, for example PLLA. Additionally, the amorphous polylactide has a biased molecular orientation in the membrane as a consequence of extrusion. Furthermore, the membrane comprises a first and a second thick portion, each thick portion having a width of about 5 mm to about 25 mm and a thickness of about 0.070 mm. The thin membrane has a thickness of about 0.02 mm as measured between the surfaces. The membrane has a viscosity property greater than about 2 g/dL, corresponding to a pre-extrusion and pre-sterilization viscosity property of greater than about 4 g/dL. Preferably, a membrane of the present invention has a viscosity property greater than about 2.75 g/dL, corresponding to pre-extrusion and pre-sterilization viscosity properties greater than about 5.5 g/dL, FIG. 2e shows such an embodiment of a membrane 150 having a first thick portion 151 forming a first edge 153, and a second thick portion 152 forming a second edge 154. Additional thick portions may be formed on additional edges or areas of the membrane 124 in other modified embodiments. For example, four thick portions may be formed on four corresponding edges of a rectangular membrane.

Figure 2F:
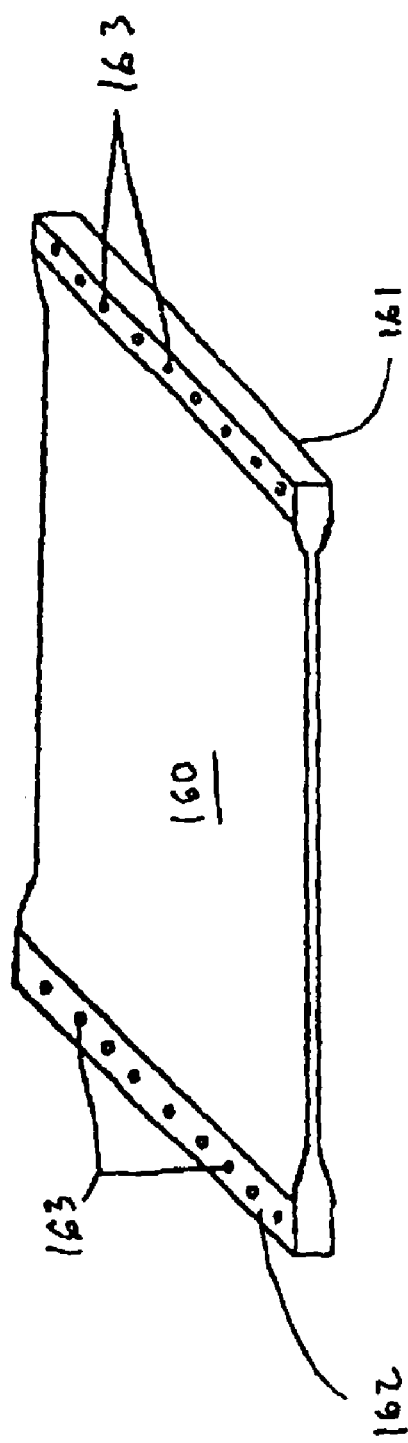

A membrane of the present invention may further comprise a plurality of holes disposed along at least one edge of the membrane. Preferably, these holes extend through the membrane. In one embodiment, the edges having the holes are formed by at least one thick portion. For example, FIG. 2f shows a membrane 160 having a first thick portion 161 and a second thick portion 162. The thick portions have holes 163 along, their lengths. The holes may facilitate for example, suturing of the thin membrane to tissue.

On the topic of attachment, various means for attaching the thin membrane to structures such as muscular tissue, other soft tissue, or bone are contemplated, and these means may be used with or without holes. According to a preferred embodiment, however, the attachment means are implemented on the actual thick portions of the thin membrane, although this is not required. In addition to sutures, staples may be used to attach the membrane to for example the paravertebral muscle. As another example, the membrane and/or the bridging membrane (described infra) may be secured to the vertebrae bone using resorbable bone screws or tacks. Tucking or folding the membrane material into anatomical crevices may be sufficient to fix either membrane's position in certain instances. An adhesive such as a fibrin sealant or a resorbable cyanoacrylate adhesive may further be utilized to secure the membranes, alone or in combination with the above means of attachment. In a preferred embodiment, the above attachment protocols are applied to the thick portions.

Figure 3A:
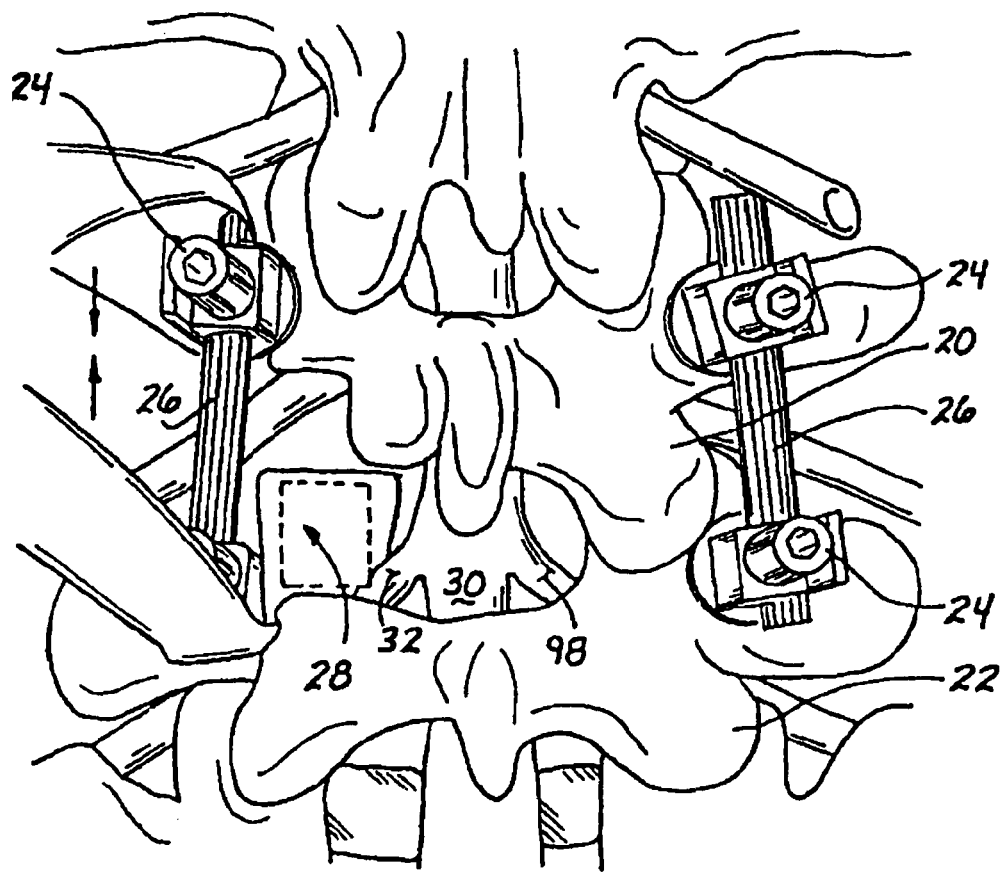
FIG. 3a illustrates a laminotomy procedure wherein a portion of the posterior arch (lamina) of a vertebra is surgically removed.

Each thick portion on the membrane may have a width for example of about 0.5 mm to about 25 mm. In one embodiment, the thick portion has a width of about 5 to about 25 mm, which may be useful for suturing purposes. In another embodiment, the thick portion has a width of about 0.5 mm, which my be useful for heat bonding as described below. In accordance with one aspect of the present invention, a thick portion can be heat bonded, such as with a bipolar electrocautery device, ultrasonically welded, or similarly seated directly to tissue, such as the dura of a spinal chord 30 and an exiting nerve root 32 (FIG. 3a). Such a device can be used to heat the membrane at various locations in addition to the thick portions, such as at non-thick edges and at points in the middle, to at least above a glass transition temperature of the membrane, and preferably above its softening point temperature. The glass transition temperature of for example PLLA is about 55° Celsius, white its softening point temperature is above 110° Celsius. The material is heated along with adjacent tissue such that the two components bond together at their interface. In another embodiment, the thick portions or other areas of the membrane can be heat bonded or sealed directly to one or both of two vertebrae 20 and 22 (FIG. 3a), or to muscle or other soft tissue, for example. In yet another embodiment, the thick portions or other areas of the thin membrane can be heat bonded or sealed directly to itself in an application, for example, wherein the membrane is wrapped around a structure and then heat joined to itself. Moreover, the technique of heat-sealing the membrane to itself or body tissue may be combined with another attachment method for enhanced anchoring. For example, the thin membrane material may be temporarily affixed in position using two or more points of heat sealing (i.e., heat welding using an electrocautery device, and sutures, staples or glue can then be added to secure the thin membrane into place.

The thin membrane of the present invention may be more effective than other membranes because it is very smooth and non-porous. For example, the tack of porosity acts to form a barrier that does not allow interaction of the tissues. The non-porosity and the smoothness of the thin membrane can reduce tissue turbulence, enhance tissue guidance, and minimize scar formation. Moreover, the smooth, uninterrupted surface of the thin membrane material may facilitate movement of the dura and local tissues across the area, hence reducing frictional rubbing and wearing which may induce scar tissue formation.

As used herein, the term "non-porous" refers to a material which is generally water tight and, in accordance with a preferred embodiment, not fluid permeable. However, in a modified embodiment of the invention micro-pores (i.e., fluid permeable but not cell permeable) may exist in the thin membrane of the present invention, to the extent, for example, that they do not substantially disrupt the smoothness of the surfaces of the resorbable thin membrane to cause scarring of tissue. In substantially modified embodiments for limited applications, pores which are cell permeable but not vessel permeable may be manufactured and used.

As presently embodied, many of the thinner membrane thicknesses can be sufficiently contoured even in the absence of heating to glass transition temperature. In one embodiment, the membranes of the present invention are capable of resorbing into the mammalian body within a period of about 18 to about 24 months from an initial implantation of the membrane into the mammalian body. The thin membranes may be used in a number of surgical applications, including: surgical repair of fracture orbital floors, surgical repair of the nasal septum and perforated ear drum thin membrane, as a protective sheathing to facilitate osteogenesis, surgical repair of the urethral anatomy and repair of urethral strictures, prevention of synostosis completed corrective surgery for cranial fusions and forearm fractures, lessening of soft-tissue fibrosis or bony growth, as a temporary covering for prenatal rupture omphalocele during staged repair procedures, guided tissue regeneration between the teeth and gingival margin, tympanic membrane repairs, dural coverings and neural repair, heart vessel repair, hernia repair, tendon anastomoses, temporary joint spacers, wound dressings, scar coverings, and as a covering for gastroschisis. The thin membrane of the present invention is particularly suitable for preventing tissue from abnormally fibrotically joining together following surgery, which can lead to abnormal scarring and interfere with normal physiological functioning. In some cases, such scarring can force and/or interfere with follow-up, corrective, or other surgical operations.

For example, there is evidence pointing to epidural adhesions as possible factors contributing to failed back surgery. Epidural fibrosis may occur following spinal injuries or as a post-operative surgical complication. The dense scar formation on dura and around nerve roots has previously been described as the "laminotomy membrane," and has been implicated in rendering subsequent spine operations technically more difficult. In a laminectomy procedure, for example, the thin membrane of the present invention is desirably inserted between the dural sleeve and the paravertebral musculature post laminotomy and conforms readily to block exposed marrow elements of the laminae. Imposition of the membrane material as a barrier between the paravertebral musculature and the epidural space is believed to reduce cellular trafficking and vascular invasion into the epidural space from the overlying muscle and adjacent exposed cancellous bone. Moreover, tests have shown that the present thin membrane does not appear to interfere with normal posterior wound healing while at the same time inhibiting the unwanted adhesions and scarring.

The very thin construction of these membranes is believed to substantially accelerate the rate of absorption of the membranes, compared to rates of absorption of thicker membrane implants of the same material. It is believed, however, that resorption into the body too quickly of the membrane will yield undesirable drops in local pH levels, thus introducing/ elevating, for example, local inflammation, discomfort and/or foreign antibody responses. Further, a resulting uneven (e.g., cracked, broken, roughened or flaked) surface of a thin membrane degrading too early may undesirably cause tissue turbulence between the tissues before, for example, adequate healing has occurred, resulting in potential tissue inflammation and scarring. It is believed that a membrane of the present invention having a thickness of about 0.200 mm or less should maintain its structural integrity for a period in excess of three weeks and, more preferably for at least 7 weeks, before substantially degrading, so that the anti-scarring function can be achieved and optimized. To the extent the membrane does not degrade at an accelerated rate, compared to a thicker membrane of the same material, the membrane should maintain its structural integrity for a period in excess of 6 months and, more preferably for at least one year, before substantially degrading, in order to achieve and optimize the anti-scarring function. The polylactide resorbable polymer thin membranes in accordance with this aspect of the present invention are thus designed to resorb into the body at a relatively slow rate.

The object of reducing acidity levels and/or tissue turbulence, and any accompanying inflammation (e.g., swelling), at the post-surgical site is believed to be of particular importance in the context of spinal surgeries, which are often performed for the very purpose of relieving inflammation-induced discomfort. It is believed that nerve tissue can be particularly sensitive to, for example, slightly elevated acidity levels and inflammation. During a typical spinal surgical procedure, such as, for example, a laminotomy, a portion of the lamina structure is removed from a patient's vertebrae in order to, for example, provide access to the spinal column and/or disk.

The thin membranes may be provided in rectangular shapes that are for example several centimeters on each side, or can be cut and formed into specific shapes, configurations and sizes by the manufacturer before packaging and sterilization. In modified embodiments, various known formulations and copolymers of for example, polylactides may affect the physical properties of the thin membrane and/or the bridging membrane (described infra). The thin membranes of the present invention are sufficiently flexible to conform around anatomical structures, although some heating in a hot water bath may be necessary for thicker configurations. In modified embodiments, certain polylactides which become somewhat more rigid and brittle at thicknesses above 0.25 mm and which can be softened by formation with other copolymers and/or other monomers, e.g., epsilon-caprolactone, for example, may be implemented to form thin membranes. Moreover, in accordance with another aspect of the present invention, the thin membrane and/or the bridging membrane (described infra) may comprises a substance for cellular control, such as at least one of a chemotactic substance for influencing cell-migration, an inhibitory substance for influencing cell-migration, mitogenic growth factor for influencing cell proliferation and a growth factor for influencing cell differentiation. Such substances may be impregnated in the membrane, but may also be coated on one or more surfaces of the membrane. In addition, substances may be contained in discrete units on or in the membrane, which may be effective to facilitate selective release of the substances when the membrane is inserted into a patient.

Figure 3B:
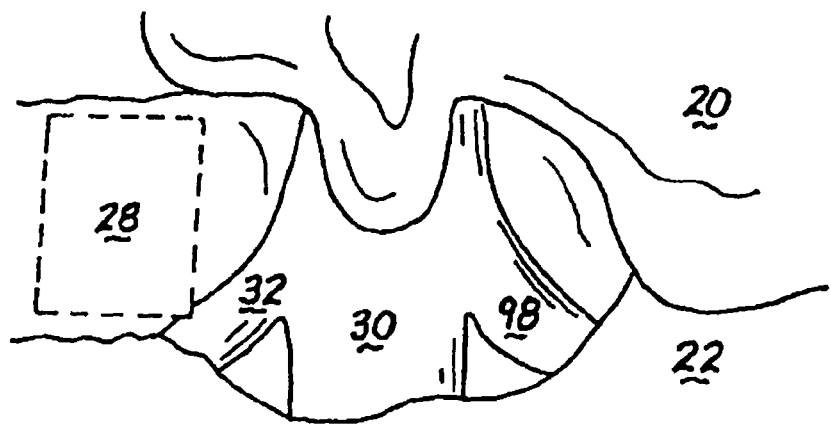

FIG. 3a illustrates a laminotomy procedure wherein two vertebrae 20 and 22 are separated and fixated using screws 24 and rods 26, and a portion of the lamina has been removed, leaving a window 28 (shown as a phantom rectangle) in the vertebrae 22. FIG. 3b is an enlarged view of the window 28 in the lamina of the vertebrae 22. The spinal chord 30 and an exiting nerve root 32 are thus exposed. In accordance with the present invention, the thin membrane is applied to the dura of both the spinal chord 30 and the exiting nerve root 32, to thereby attenuate or eliminate the occurrence of post-operative scarring in the vicinity of the exiting nerve root 32.

In a modified embodiment, a thicker bridging membrane is applied to one or both of the vertebrae 20 and 22, to thereby bridge (i.e., tent) over and cover the window 28. This bridging membrane may be non-porous, fluid permeable, cell permeable or vessel permeable in accordance with various embodiments, and preferably comprises a thickness between about 0.5 mm and 2.0 mm for preventing prolapse of adjacent muscle tissue into the foramen (i.e., the spinal lumen containing the spinal chord 30 and exiting nerve root 32). In accordance with various embodiments, the bridging membrane may be used alone or in combination with the scar-reduction resorbable barrier micro-membrane or, the scar-reduction resorbable barrier membrane may be used without the bridging membrane.

Turning to FIG. 3c, a pre-formed thin membrane 34 is formed with a first welding flange 36 and a second welding flange 38 thereon. The welding flanges can be constructed to be thick portions or to have thick portions merely along their edges. Moreover, in modified embodiments thick portions may be formed on other edges of the below-described membranes, on other portions of the membranes, and/or any combinations thereof. A trunk portion 40 fits over the spinal chord 30, and a branch portion 42 fits over the exiting nerve root 32. The first welding flange 36 is formed by a first slit 44 and a second slit 46, and the second welding flange 38 is formed by a first slit 48 and a second slit 50. In application, the pre-formed thin membrane 34 is placed over the spinal chord 30 and the exiting nerve root 32 and, subsequently, the first welding flange 36 and the second welding flange 38 are bent at least partially around the exiting nerve root. The rounded end 52 of the branch portion 42 fits onto a portion of the exiting nerve root 32 furthest away from the spinal chord 30. As presently embodied, the first welding flange 36 and the second welding flange are wrapped around, and preferably tucked beneath (i.e., behind) the exiting nerve root 32. In a preferred embodiment, the first welding flange 36 is then heat welded to the second welding flange 38. The flanges preferably are cut to wrap entirely around the exiting nerve root 32 and overlap one another. The first welding flange 36 may be sutured to the second welding flange 38, alone or in addition with the heat welding step, to thereby secure the first welding flange 36 to the second welding flange 38. In another embodiment, neither heat welding nor suturing are used and the flanges are merely tucked partially or completely around the exiting nerve root 32 (depending on the dimensions of the root 32). When sutures are to be used, the pre-formed thin membrane 34 may be pre-formed and packaged with optional suture apertures 60. The edges 64 and 66 are then preferably heat welded to the spinal chord 30. The two edges 68 and 70 form a third welding flange 72. A fourth welding flange 74 is formed by slits 76 and 78, and a fifth welding flange 80 is formed by slits 82 and 84. The welding flanges may be secured in manners similar to those discussed in connection with the welding flanges 36 and 38. Heat welds may further be secured along other edges and along the surface of the pre-formed thin membrane 34. Moreover, notches may be formed on the membranes of the present invention, such as, for example, at the ends 64 and 66 in modified-shape embodiments, for accommodating, for example, the spinal processes.

FIG. 4 illustrates a thin membrane for application to two exiting nerve roots 32 and 98 of the spinal chord in accordance with another pre-formed embodiment of the present invention. FIG. 5 illustrates a thin membrane similar to that of FIG. 4 but adapted for application to four exiting nerve roots of the spinal chord in accordance with another pre-formed embodiment of the present invention. For example, the branch portion 100 is analogous in structure and operation to the branch portion 42 of the FIG. 3 embodiment, and the other branch portion 102 is constructed to accommodate the exiting nerve root 98. Similar elements are shown in FIG. 5 at 100a, 102a, 100b and 102c. Other configurations for accommodating different anatomical structures may be formed. For example, configurations may be designed to be formed into, for example, cone structures to fit around base portions with protrusions extending through the centers of the membranes. Suture perforations may be formed around perimeters of the membranes, and cell and vessel permeable pores may be included as well.

In accordance with the present invention, the pre-formed thin membranes are preformed and sealed in sterilized packages for subsequent use by the surgeon. Since one objective of the thin membranes of the present invention is to reduce sharp edges and surfaces, preformation of the membranes is believed to help facilitate, albeit to a relatively small degree, rounding of the edges for less rubbing, tissue turbulence and inflammation. That is, the surfaces and any sharp edges of the thin membranes are believed to be capable of slightly degrading over time in response to exposure of the membranes to moisture in the air, to thereby form rounder edges. This is believed to be an extremely minor effect. Moreover, any initial heating to glass temperature of the pre-cut membranes just before implanting can further round any sharp edges. Moreover, the very thin membranes of the present invention may be particularly susceptible to these phenomena, and, perhaps to a more noticeable extent, are susceptible to tearing or damage from handling, thus rendering the pre-forming of the thin membranes beneficial for preserving the integrity thereof.

The above-described embodiments have been provided by way of example, and the present invention is not limited to these examples. While the foregoing is a complete description of the preferred embodiments of the invention, various alternatives, modifications, and equivalents may be used. Moreover, it will be apparent that certain other modifications may be practiced within the scope of the appended claims.

What is claimed is:
1. A system, comprising:
a resorbable scar reduction membrane for attenuating a formation of post-surgical scar tissue between a healing post-surgical site and adjacent surrounding tissue following an in vivo surgical procedure on the post-surgical site, the resorbable scar reduction membrane having a pre-implant configuration that is defined as a configuration of the implant immediately before the implant is formed between the post-surgical site and the adjacent surrounding tissue, the resorbable scar reduction membrane having a first substantially-smooth side and a second substantially-smooth side; the resorbable scar reduction membrane comprising a layer of resorbable polymer base material between the first substantially-smooth side and the second substantially-smooth side, the layer of resorbable polymer base material having a substantially uniform composition, a thickness of the layer of resorbable polymer base material, measured between the first substantially-smooth side and the second substantially-smooth side, being between 10 microns and 300 microns; and another membrane, which comprises a thickness less than 2000 microns and which is permeable.

2. The system as set forth in claim 1, wherein the resorbable polymer base material comprises a polymer consisting essentially of one or more of a lactide polymer, a copolymer of two or more cyclic esters, and glycol.

3. The system as set forth in claim 1, wherein the resorbable polymer base material is a copolymer comprising L-lactide and DL-lactide.

4. The system as set forth in claim 1, wherein the other membrane is a bridging membrane.

5. The system as set forth in claim 1, wherein the thickness of the layer of resorbable polymer base material is 200 microns or less.

6. The system as set forth in claim 1, wherein the layer of resorbable polymer base material is not permeable.

7. The system as set forth in claim 1, wherein the resorbable scar reduction membrane is impregnated with at least one of a chemotactic substance for influencing cell-migration, an inhibitory substance for influencing cell-migration, a mitogenic growth factor for influencing cell proliferation, a growth factor for influencing cell differentiation.

8. The system as set forth in claim 1, wherein the resorbable scar reduction membrane consists essentially of a single layer of resorbable polymer base material between the first substantially-smooth side and the second substantially-smooth side.

9. The system as set forth in claim 1, wherein the resorbable scar reduction membrane comprises a plurality of holes disposed along an edge of the resorbable scar reduction membrane.

10. The system as set forth in claim 9, wherein the edge extends around the resorbable scar reduction membrane.

11. The system as set forth in claim 1, wherein the resorbable scar reduction membrane does not comprise any holes substantially away from the edge of the resorbable scar reduction membrane.

12. The system as set forth in claim 1, wherein at least one slit is formed in a periphery of the resorbable scar reduction membrane so that the edge extends along the slit.

13. The system as set forth in claim 1, wherein:
the resorbable scar reduction membrane further comprises a plurality of holes disposed away from the edge;
each of the holes near the periphery has a first diameter;
each of the holes near the center has a second diameter; and
the first diameters are greater than the second diameters.

14. The system as set forth in claim 1, wherein a plurality of slits are formed in a periphery of the resorbable scar reduction membrane so that the edge extends along the slit.

15. The system as set forth in claim 1, wherein the resorbable scar reduction membrane comprises at least one slit disposed in the layer of resorbable polymer base material.

16. The system as set forth in claim 1, wherein the resorbable scar reduction membrane is sealed in a sterile packaging.

17. The system as set forth in claim 1, wherein the resorbable scar reduction membrane is cut to have at least one tab.

18. The system as set forth in claim 1, wherein the resorbable scar reduction membrane comprises at least one notch disposed in the layer of resorbable polymer base material.

19. The system as set forth in claim 1, wherein the resorbable scar reduction membrane comprises a plurality of notches disposed in the layer of resorbable polymer base material.

20. The system as set forth in claim 1, wherein the layer of resorbable polymer base material consists essentially of a material selected from the group consisting of:
a poly-betide; and
a copolymer of two or more lactides.

* * * * *